United States Patent
Ostroff

(10) Patent No.: US 9,522,284 B2
(45) Date of Patent: Dec. 20, 2016

(54) DEFIBRILLATION PACING CIRCUITRY

(71) Applicant: CAMERON HEALTH INC, St. Paul, MN (US)

(72) Inventor: Alan H. Ostroff, Pleasanton, CA (US)

(73) Assignee: CAMERON HEALTH INC., St. Paul, MN (US)

( * ) Notice: Subject to any disclaimer, the term of this patent is extended or adjusted under 35 U.S.C. 154(b) by 0 days.

(21) Appl. No.: 15/051,805

(22) Filed: Feb. 24, 2016

(65) Prior Publication Data

US 2016/0166841 A1 Jun. 16, 2016

Related U.S. Application Data

(63) Continuation of application No. 12/426,779, filed on Apr. 20, 2009, now Pat. No. 9,283,398, which is a continuation of application No. 11/146,607, filed on Jun. 7, 2005, now Pat. No. 7,522,957, which is a continuation of application No. 10/011,955, filed on Nov. 5, 2001, now Pat. No. 6,952,608.

(51) Int. Cl.
*A61N 1/39* (2006.01)
*A61N 1/362* (2006.01)

(52) U.S. Cl.
CPC .............. *A61N 1/3962* (2013.01); *A61N 1/362* (2013.01); *A61N 1/3912* (2013.01)

(58) Field of Classification Search
CPC ... A61N 1/3962; A61N 1/3912; A61N 1/3918
See application file for complete search history.

(56) References Cited

U.S. PATENT DOCUMENTS

| | | |
|---|---|---|
| 3,653,387 A | 4/1972 | Ceier |
| 3,710,374 A | 1/1973 | Kelly |
| 4,191,942 A | 3/1980 | Long |
| 4,223,678 A | 9/1980 | Langer et al. |
| 4,402,322 A | 9/1983 | Duggan |
| 4,407,288 A | 10/1983 | Langer et al. |
| 4,567,900 A | 2/1986 | Moore |
| 4,602,637 A | 7/1986 | Elmqvist et al. |
| 4,603,705 A | 8/1986 | Speicher et al. |
| 4,693,253 A | 9/1987 | Adams |

(Continued)

FOREIGN PATENT DOCUMENTS

| | | |
|---|---|---|
| EP | 0316616 A2 | 5/1989 |
| EP | 0347353 A1 | 12/1989 |

(Continued)

OTHER PUBLICATIONS

Bardy et al., "Multicenter Experience with a Pectoral Unipolar Implantable Cardioverter-Defibrillator", JACC, vol. 28(2), pp. 400-410, Aug. 1996.

(Continued)

*Primary Examiner* — George Evanisko
(74) *Attorney, Agent, or Firm* — Seager, Tufte & Wickhem LLP

(57) ABSTRACT

Electrical circuit componentry is switchable into a defibrillator circuit to deliver a constant pacing current to a patient. The circuitry may include a constant current source inserted in a leg of the defibrillator circuit or a resistor of selected value inserted between a high voltage source and the high side of a defibrillator circuit.

4 Claims, 3 Drawing Sheets

(56) References Cited

U.S. PATENT DOCUMENTS

| | | | |
|---|---|---|---|
| 4,800,883 | A | 1/1989 | Winstrom |
| 4,830,005 | A | 5/1989 | Woskow |
| 4,944,300 | A | 7/1990 | Saksena |
| 5,105,810 | A | 4/1992 | Collins et al. |
| 5,109,842 | A | 5/1992 | Adinolfi |
| 5,129,392 | A | 7/1992 | Bardy et al. |
| 5,133,353 | A | 7/1992 | Hauser |
| 5,144,946 | A | 9/1992 | Weinberg et al. |
| 5,184,616 | A | 2/1993 | Weiss |
| 5,261,400 | A | 11/1993 | Bardy |
| 5,331,966 | A | 7/1994 | Bennett et al. |
| 5,342,407 | A | 8/1994 | Dahl et al. |
| 5,376,103 | A | 12/1994 | Anderson et al. |
| 5,376,104 | A | 12/1994 | Sakai et al. |
| 5,411,547 | A | 5/1995 | Causey, III |
| 5,413,591 | A | 5/1995 | Knoll |
| 5,476,503 | A | 12/1995 | Yang |
| 5,507,781 | A | 4/1996 | Kroll et al. |
| 5,531,765 | A | 7/1996 | Pless |
| 5,601,607 | A | 2/1997 | Adams |
| 5,603,732 | A | 2/1997 | Dahl et al. |
| 5,618,287 | A | 4/1997 | Fogarty et al. |
| 5,620,477 | A | 4/1997 | Pless et al. |
| 5,645,572 | A | 7/1997 | Kroll et al. |
| 5,658,317 | A | 8/1997 | Haefner et al. |
| 5,658,321 | A | 8/1997 | Fayram et al. |
| 5,674,260 | A | 10/1997 | Weinberg |
| 5,690,683 | A | 11/1997 | Haefner et al. |
| 5,697,953 | A | 12/1997 | Kroll et al. |
| 5,713,926 | A | 2/1998 | Hauser et al. |
| 5,718,242 | A | 2/1998 | McClure et al. |
| 5,766,226 | A | 6/1998 | Pedersen |
| 5,836,976 | A | 11/1998 | Min et al. |
| 5,919,211 | A | 7/1999 | Adams |
| 5,935,154 | A | 8/1999 | Westlund |
| 5,941,904 | A | 8/1999 | Johnston et al. |
| 6,014,586 | A | 1/2000 | Weinberg et al. |
| 6,026,325 | A | 2/2000 | Weinberg et al. |
| 6,058,328 | A | 5/2000 | Levine et al. |
| 6,096,063 | A | 8/2000 | Lopin et al. |
| 6,104,953 | A * | 8/2000 | Leyde ............... A61N 1/39 607/4 |
| 6,128,531 | A * | 10/2000 | Campbell-Smith .. A61N 1/3706 607/5 |
| 6,144,866 | A | 11/2000 | Miesel et al. |
| 6,169,921 | B1 | 1/2001 | KenKnight et al. |
| 6,185,450 | B1 | 2/2001 | Seguine et al. |
| 6,208,895 | B1 * | 3/2001 | Sullivan ............ A61N 1/39 607/4 |
| 6,241,751 | B1 | 6/2001 | Morgan et al. |
| 6,411,844 | B1 | 6/2002 | Kroll et al. |
| 6,647,292 | B1 | 11/2003 | Bardy et al. |
| 6,721,597 | B1 | 4/2004 | Bardy et al. |
| 6,778,860 | B2 | 8/2004 | Ostroff et al. |
| 6,788,974 | B2 | 9/2004 | Bardy et al. |
| 6,856,835 | B2 | 2/2005 | Bardy et al. |
| 6,866,044 | B2 | 3/2005 | Bardy et al. |
| 6,937,907 | B2 | 8/2005 | Bardy et al. |
| 6,950,705 | B2 | 9/2005 | Bardy et al. |
| 6,952,608 | B2 | 10/2005 | Ostroff |
| 6,954,670 | B2 | 10/2005 | Ostroff |
| 7,039,465 | B2 | 5/2006 | Bardy et al. |
| 7,065,407 | B2 | 6/2006 | Bardy et al. |
| 7,069,080 | B2 | 6/2006 | Bardy et al. |
| 7,146,212 | B2 | 12/2006 | Bardy et al. |
| 7,389,139 | B2 | 6/2008 | Ostroff |
| 2001/0027330 | A1 | 10/2001 | Sullivan et al. |
| 2003/0088283 | A1 | 5/2003 | Ostroff |

FOREIGN PATENT DOCUMENTS

| | | |
|---|---|---|
| EP | 0518599 A2 | 12/1992 |
| EP | 0641573 A2 | 3/1995 |
| EP | 0641573 A3 | 6/1997 |
| EP | 0518599 B1 | 9/1997 |
| EP | 0536873 B1 | 9/1997 |
| EP | 0917887 A1 | 5/1999 |
| EP | 0923130 A1 | 6/1999 |
| WO | 9319809 A1 | 10/1993 |
| WO | 9825349 A1 | 6/1998 |
| WO | 9903534 A1 | 1/1999 |
| WO | 9937362 A1 | 7/1999 |
| WO | 0156166 A2 | 8/2001 |
| WO | 0222208 A2 | 3/2002 |
| WO | 0224275 A2 | 3/2002 |
| WO | 0224275 A3 | 5/2002 |
| WO | 0222208 A3 | 6/2002 |
| WO | 02068046 A1 | 9/2002 |
| WO | 03018121 A2 | 3/2003 |

OTHER PUBLICATIONS

Friedman et al., "Implantable Defibrillators in Children: From Whence to Shock," Journal of Cardiovascular Electrophysiology, vol. 12(3), pp. 361-362, Mar. 2001.

Gradaus et al., "Nonthoracotomy Implantable Cardioverter Defibrillator Placement in Children: Use of Subcutaneous Array Leads and Abdominally Placed Implantable Cardiovascular Defibrillators in Children," Journal of Cardiovascular Electrophysiology, vol. 12(3) pp. 356-360, Mar. 2001.

Higgins et al., "The First Year Experience with the Dual Chamber ICD," PACE, vol. 23, pp. 18-25, Jan. 2000.

Mirowski et al., "Automatic Detection and Defibrillation of Lethal, Arrhythmias—A new Concept," JAMA, vol. 213(4), pp. 615-616, Jul. 27, 1970.

Olson et al., "Onset and Stability for Ventricular Tachyarrhythmia Detection in an Implantable Pacer-Cardioverter-Defibrillator," IEEE, pp. 167-170, 1987.

Schuder et al., "Experimental Ventricular Defibrillation with an Automatic and Completely Implanted System," Trans. Amer. Soc. Artif. Int. Organs, vol. XVI, pp. 207-212, 1970.

Schuder, "The role of an Engineering Oriented Medical Research Group in Developing Improved Methods and Devices for Achieving Ventricular Defibrillation: The University of Missouri Experience," PACE, vol. 16, pp. 95-123, Jan. 1993.

Schuder et al., "Standby Implanted Defibrillators," Arch Intern. Med., vol. 127, p. 317 (single sheet), Feb. 1971.

Schuder et al., "Transthoracic Ventricular Defibrillation in the Dog with Truncated and Untruncated Exponential Stimuli," IEEE Transactions of Bio-Medical Engineering, vol. BME 18(6).

Schwacke et al., "Komplikationen mit Sonden bei 340 Patienten mit einem Implantierbaren Kardioverter/Defibrillator," Z Kardiol, vol. 88(8), pp. 559-565, 1999.

Tietze et al., "Halbleiter-Schaltungstechnik," Springer-Verlag, Berlin, Germany, pp. 784-786, 1991.

Valenzuela et al., "Outcomes of Rapid Defibrillation by Security Offices After Cardiac Arrest in Casinos," The New England Journal of Medicine, vol. 343(17), pp. 1206-1209, Oct. 26, 2000.

Walters et al., "Analog to Digital Conversion Techniques in Implantable Devices," Annual Internaational Conference of the IEEE Engineering in Medicine and Biology Society, vol. 13(4), pp. 1674-1676, 1991.

* cited by examiner

DEFIBRILLATION PACING CIRCUITRY

RELATED APPLICATIONS

This application is a continuation of U.S. patent application Ser. No. 12/426,779, filed Apr. 20, 2009 and titled DEFIBRILLATION PACING CIRCUITRY, now U.S Patent No. 9,283,398, which is a continuation of U.S. patent application Ser. No. 11/146,607, filed Jun. 7, 2005, now U.S. Pat. No. 7,522,957 and titled DEFIBRILLATION PACING CIRCUITRY, which is a continuation of U.S. patent application Ser. No. 10/011,955, filed Nov. 5, 2001, now U.S. Pat. No. 6,952,608 and titled DEFIBRILLATION PACING CIRCUITRY, the entire disclosures of which are incorporated herein by reference.

The invention of the present application may find application in systems such as is disclosed in U.S. Pat. No. 6,721,597, titled SUBCUTANEOUS ONLY IMPLANTABLE CARDIOVERTER-DEFIBRILLATOR AND OPTIONAL PACER, and U.S. Pat. No. 6,647,292, titled UNITARY SUBCUTANEOUS ONLY IMPLANTABLE CARDIOVERTER-DEFIBRILLATOR AND OPTIONAL PACER, and the disclosures of both applications are hereby incorporated by reference.

In addition, the foregoing applications are related to: [0004] U.S. patent application Ser. No. 09/940,283, filed Aug. 27, 2001, now U.S. Pat. No. 7,065,407 and titled DUCKBILL-SHAPED IMPLANTABLE CARDIOVERTER-DEFIBRILLATOR CANISTER AND METHOD OF USE; [0005] U.S. patent application Ser. No. 09/940,371, filed Aug. 27, 2001, now U.S. Pat. No. 7,039,465 and titled CERAMICS AND/OR OTHER MATERIAL INSULATED SHELL FOR ACTIVE AND NON-ACTIVE S-ICD CAN; [0006] U.S. patent application Ser. No. 09/940,468, filed Aug. 27, 2001, published as US 2002-0035379 A1 and titled SUBCUTANEOUS ELECTRODE FOR TRANSTHORACIC CONDUCTION WITH IMPROVED INSTALLATION CHARACTERISTICS; [0007] U.S. patent application Ser. No. 09/941,814, filed Aug. 27, 2001, published as US 2002-0035381 A1 and titled SUBCUTANEOUS ELECTRODE WITH IMPROVED CONTACT SHAPE FOR TRANSTHORACIC CONDUCTION; [0008] U.S. patent application Ser. No. 09/940,356, filed Aug. 27, 2001, published as US 2002-0035378 A1 and titled SUBCUTANEOUS ELECTRODE FOR TRANSTHORACIC CONDUCTION WITH HIGHLY MANEUVERABLE INSERTION TOOL; [0009] U.S. patent application Ser. No. 09/940,340, filed Aug. 27, 2001, now U.S. Pat. No. 6,937,907 and titled SUBCUTANEOUS ELECTRODE FOR TRANSTHORACIC CONDUCTION WITH LOW-PROFILE INSTALLATION APPENDAGE AND METHOD OF DOING SAME; [0010] U.S. patent application Ser. No. 09/940,287, filed Aug. 27, 2001, published as US 2002-0035377 A1 and titled SUBCUTANEOUS ELECTRODE FOR TRANSTHORACIC CONDUCTION WITH INSERTION TOOL; [0011] U.S. patent application Ser. No. 09/940,377, filed Aug. 27, 2001, now U.S. Pat. No. 6,866,044 and titled METHOD OF INSERTION AND IMPLANTATION OF IMPLANTABLE CARDIOVERTER-DEFIBRILLATOR CANISTERS; [0012] U.S. patent application Ser. No. 09/940,599, filed Aug. 27, 2001, now U.S. Pat. No. 6,950,705 and titled CANISTER DESIGNS FOR IMPLANTABLE CARDIOVERTER-DEFIBRILLATORS; [0013] U.S. patent application Ser. No. 09/940,373, filed Aug. 27, 2001, now U.S. Pat. No. 6,788,974 and titled RADIAN CURVE SHAPED IMPLANTABLE CARDIOVERTER-DEFIBRILLATOR CANISTER; [0014] U.S. patent application Ser. No. 09/940,273, filed Aug. 27, 2001, now U.S. Pat. No. 7,069,080 and titled CARDIOVERTER-DEFIBRILLATOR HAVING A FOCUSED SHOCKING AREA AND ORIENTATION THEREOF; [0015] U.S. patent application Ser. No. 09/940,378, filed Aug. 27, 2001, now U.S. Pat. No. 7,146,212 and titled BIPHASIC WAVEFORM FOR ANTI-BRADYCARDIA PACING FOR A SUBCUTANEOUS IMPLANTABLE CARDIOVERTER-DEFIBRILLATOR; and [0016] U.S. patent application Ser. No. 09/940,266, filed Aug. 27, 2001, now U.S. Pat. No. 6,856,835 and titled BIPHASIC WAVEFORM FOR ANTI-TACHYCARDIA PACING FOR A SUBCUTANEOUS IMPLANTABLE CARDIOVERTER-DEFIBRILLATOR, the entire disclosures of which are incorporated herein by reference.

FIELD

The present invention relates to apparatus and methods useful in connection with performing electrical cardioversion/defibrillation and optional pacing of the heart.

BACKGROUND

Defibrillation/cardioversion is a technique employed to counter arrhythmic heart conditions including some tachycardias in the atria and/or ventricles. Typically, electrodes are employed to stimulate the heart with electrical impulses or shocks, of a magnitude substantially greater than pulses used in cardiac pacing.

Defibrillation/cardioversion systems include body implantable electrodes that are connected to a hermetically sealed container housing the electronics, battery supply and capacitors. The entire system is referred to as implantable cardioverter/defibrillators (ICDs). The electrodes used in ICDs can be in the form of patches applied directly to epicardial tissue, or, more commonly, are on the distal regions of small cylindrical insulated catheters that typically enter the subclavian venous system, pass through the superior vena cava and, into one or more endocardial areas of the heart. Such electrode systems are called intravascular or transvenous electrodes. U.S. Pat. Nos. 4,603,705; 4,693,253; 4,944,300; and 5,105,810, the disclosures of which are all incorporated herein by reference, disclose intravascular or transvenous electrodes, employed either alone, in combination with other intravascular or transvenous electrodes, or in combination with an epicardial patch or subcutaneous electrodes. Compliant epicardial defibrillator electrodes are disclosed in U.S. Pat. Nos. 4,567,900 and 5,618,287, the disclosures of which are incorporated herein by reference. A sensing epicardial electrode configuration is disclosed in U.S. Pat. No. 5,476,503, the disclosure of which is incorporated herein by reference.

In addition to epicardial and transvenous electrodes, subcutaneous electrode systems have also been developed. For example, U.S. Pat. Nos. 5,342,407 and 5,603,732, the disclosures of which are incorporated herein by reference, teach the use of a pulse monitor/generator surgically implanted into the abdomen and subcutaneous electrodes implanted in the thorax. This system is far more complicated to use than current ICD systems using transvenous lead systems together with an active can electrode and therefore it has no practical use. It has in fact never been used because of the surgical difficulty of applying such a device (3 incisions), the impractical abdominal location of the generator and the electrically poor sensing and defibrillation aspects of such a system.

Recent efforts to improve the efficiency of ICDs have led manufacturers to produce ICDs which are small enough to be implanted in the pectoral region. In addition, advances in circuit design have enabled the housing of the ICD to form a subcutaneous electrode. Some examples of ICDs in which the housing of the ICD serves as an optional additional electrode are described in U.S. Pat. Nos. 5,133,353; 5,261,400; 5,620,477; and 5,658,321, the disclosures of which are incorporated herein by reference.

ICDs are now an established therapy for the management of life threatening cardiac rhythm disorders, primarily ventricular fibrillation (V-Fib). ICDs are very effective at treating V-Fib, but are therapies that still require significant surgery.

As ICD therapy becomes more prophylactic in nature and used in progressively less ill individuals, especially children at risk of cardiac arrest, the requirement of ICD therapy to use intravenous catheters and transvenous leads is an impediment to very long term management as most individuals will begin to develop complications related to lead system malfunction sometime in the 5-10 year time frame, often earlier. In addition, chronic transvenous lead systems, their reimplantation and removals, can damage major cardiovascular venous systems and the tricuspid valve, as well as result in life threatening perforations of the great vessels and heart. Consequently, use of transvenous lead systems, despite their many advantages, are not without their chronic patient management limitations in those with life expectancies of >5 years. The problem of lead complications is even greater in children where body growth can substantially alter transvenous lead function and lead to additional cardiovascular problems and revisions. Moreover, transvenous ICD systems also increase cost and require specialized interventional rooms and equipment as well as special skill for insertion. These systems are typically implanted by cardiac electrophysiologists who have had a great deal of extra training.

In addition to the background related to ICD therapy, the present invention requires a brief understanding of a related therapy, the automatic external defibrillator (AED) AEDs employ the use of cutaneous patch electrodes, rather than implantable lead systems, to effect defibrillation under the direction of a bystander user who treats the patient suffering from V-Fib with a portable device containing the necessary electronics and power supply that allows defibrillation. AEDs can be nearly as effective as an ICD for defibrillation if applied to the victim of ventricular fibrillation promptly, i.e., within 2 to 3 minutes of the onset of the ventricular fibrillation.

AED therapy has great appeal as a tool for diminishing the risk of death in public venues such as in air flight. However, an AED must be used by another individual, not the person suffering from the potential fatal rhythm. It is more of a public health tool than a patient-specific tool like an ICD. Because >75% of cardiac arrests occur in the home, and over half occur in the bedroom, patients at risk of cardiac arrest are often alone or asleep and can not be helped in time with an AED. Moreover, its success depends to a reasonable degree on an acceptable level of skill and calm by the bystander user.

What is needed therefore, especially for children and for prophylactic long term use for those at risk of cardiac arrest, is a combination of the two forms of therapy which would provide prompt and near-certain defibrillation, like an ICD, but without the long-term adverse sequelae of a transvenous lead system while simultaneously using most of the simpler and lower cost technology of an AED. What is also needed is a cardioverter/defibrillator that is of simple design and can be comfortably implanted in a patient for many years.

Moreover, it has appeared advantageous to the inventor to provide the capability in such improved circuitry to provide a signal suitable for pacing when the circuitry is not operating in a defibrillation mode.

SUMMARY

Accordingly, the invention relates in various aspects to methods and apparatus for selectively converting a defibrillator circuit or circuit for delivering a defibrillating pulse to a patient into circuitry suitable for providing a constant current, useful, e.g., in pacing applications.

BRIEF DESCRIPTION OF THE DRAWINGS

For a better understanding of the invention, reference is now made to the drawings where like numerals represent similar objects throughout the figures and wherein.

DETAILED DESCRIPTION

Figure 1:
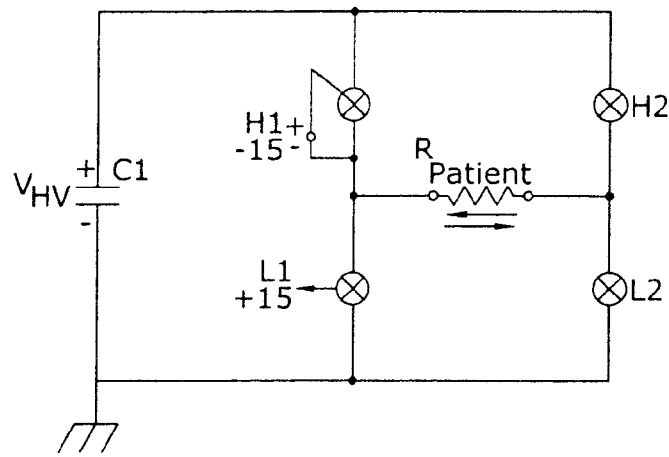
FIG. 1 is a schematic view of a conventional defibrillator circuit.

FIG. 1 illustrates a conventional "H-bridge" defibrillator circuit 11. The circuit 11 includes a capacitor $C_1$ which is charged to a high voltage $V_{HV}$ and four switches $H_1$, $H_2$, $L_1$, $L_2$. The capacitor $C_1$ and switches $H_1$, $H_2$, $L_1$, $L_2$ are used to create either a monophasic voltage pulse or a biphasic voltage pulse (FIG. 2) across a patient represented by resistance $R_{PATIENT}$. In various applications, the switches $H_1$, $H_2$, $L_1$, $L_2$, may be MOSFETs, IGBTs, or SCRs (silicon controlled rectifiers).

Figure 2:
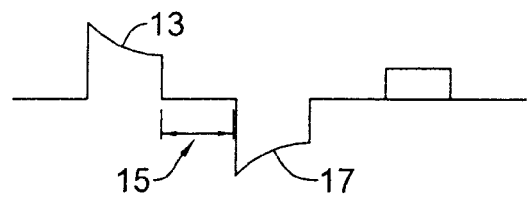
FIG. 2 is a circuit schematic of an illustrative embodiment of the present invention.

To create a biphasic waveform such as that shown in FIG. 2, a first pair of switches, e.g., $H_1$ and $L_2$, may be closed to create a positive pulse 13. Then all of the switches, $H_1$, $H_2$, $L_1$, $L_2$, are turned off during a "center pulse" delay period $d_1$. At the end of the delay period $d_1$, the switches $H_2$ and $L_1$ are both closed, thereby reversing the current through the patient $R_{PATIENT}$ to produce a negative voltage pulse 17. Typically, digital logic is employed to control the sequencing of the switches $H_1$, $H_2$, $L_1$, $L_2$. In such cases, the order of the pulses can be inverted, i.e., the negative pulse 17 can be produced before the positive pulse 13. In illustrative applications, the duration of the pulses 13, 17 is, e.g., 1 to 20 milliseconds and the inter-pulse delay $d_1$ is, e.g., one millisecond.

Figure 3:
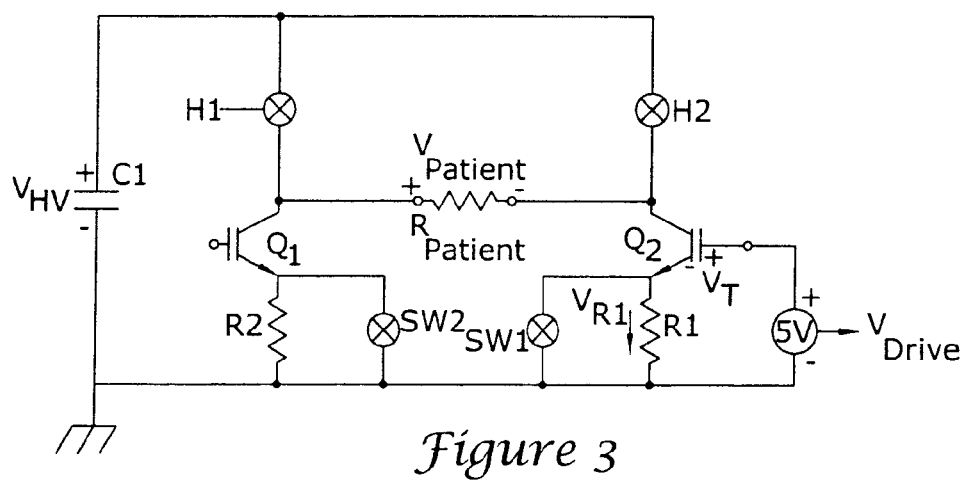
FIG. 3 is a circuit schematic of an alternate embodiment.

FIG. 3 illustrates circuitry which may operate as a defibrillator circuit during a first selected interval and as a constant current source during a second selected interval. The constant current may be useful, for example, in providing a "pacing" current to a patient $R_{PATIENT}$.

As in FIG. 1, the high side switches $H_1$, $H_2$ employed in FIG. 3 may be IGBTs, MOSFETs, SCRs, or other suitable switches. Such high side switches $H_1$, H₂ may be controlled in any suitable manner such as, for example, with pulse transformers, opto-couplers, photovoltaic generators, or in accordance with the teachings of U.S. patent application Ser. No. 10/011,957, filed on Nov. 5, 2001 on behalf of the same inventor, now U.S. Pat. No. 6,954,670 and titled SIMPLIFIED DEFIBRILLATOR OUTPUT CIRCUIT, herein incorporated by reference. Digital logic suitable for controlling such circuitry to achieve switching may comprise a programmed microprocessor, microcontroller, discrete logic, or other forms of digital logic control.

In the circuit of FIG. 3, a resistor $R_1$ is inserted in series with the emitter or the source leg of a first low side transistor $Q_2$, which is preferably an IGBT or MOSFET. Similarly, a resistor $R_2$ is inserted in series with the emitter or source leg of the second low side transistor $Q_1$. A constant voltage is applied across the resistor $R_1$ via a voltage source, which applies a voltage $V_{DRIVE}$ to the gate (or base) of the first low side transistor $Q_2$. During operation of the circuit of FIG. 2 as a defibrillator, the transistors $Q_1$, $Q_2$ serve the purposes of low side switches, e.g., $L_1$, $L_2$ of FIG. 1, and the resistors $R_1$, $R_2$ are switched out of the circuit by suitable means, e.g., switches $SW_1$ and $SW_2$. During pacing operation of the circuit of FIG. 3, a suitable switching signal is applied to switch resistor $R_1$ into the circuit.

In an illustrative application of the circuitry of FIG. 3, the low side transistors $Q_1$, $Q_2$ may be high voltage IGBTs or MOSFETs, ranging from 500 volts to 3,000 volts capacity or greater. In the circuit of FIG. 3, the voltage across the resistor $R_1$ is defined by the equation:

$$V_{R1} = V_{DRIVE} - V_T \quad (1)$$

where $V_T$ is the fixed (constant) threshold voltage of the low side transistor $Q_1$. Thus, if $V_{DRIVE}$ is 15 volts, and $V_T$ is in the range of 2-6 volts, $V_{R1}$ is in the range of 13 to 9 volts. Accordingly, a constant voltage is applied across the resistor $R_1$, resulting in a constant current $I_{R1}$ through the resistor $R_1$, and hence through the patient $R_{PATIENT}$.

As those skilled in the art may appreciate, the threshold voltage $V_T$ of the transistor $Q_1$ may vary from device to device. Hence, it is typically necessary to calibrate the circuit in production. In calibrating a circuit like that of FIG. 3, a known voltage is applied and the current through $R_1$ is measured, typically resulting in a large offset, which is compensated for by the system software.

Figure 4:
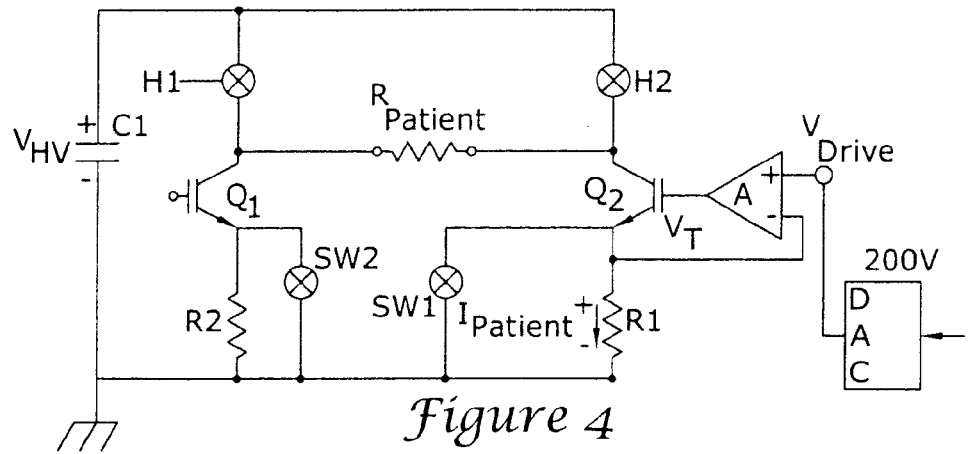
FIG. 4 is a circuit schematic of a second alternate embodiment.

In order to avoid calibration, the voltage source may be constructed using a feedback circuit employing an operational amplifier as shown in FIG. 4. The op-amp is connected to directly drive the low side transistor $Q_2$, which may comprise, e.g., a MOSFET or IGBT. Use of the operational amplifier removes the uncertainty of the threshold voltage $V_T$ so that the current that passes through the resistor $R_1$ is equal to simply $V_{DRIVE}$ divided by $R_1$. Thus, one can either drive the transistor $Q_2$ with a voltage source and calibrate the system for the $V_T$ of the transistor $Q_2$ or use an op-amp circuit to remove the error created by the threshold voltage $V_T$ of the transistor $Q_2$.

During constant current source operation of the circuit of FIG. 4, the appropriate high side switch is on to permit current flow. In addition, the capacitor voltage $V_c$ needs to be appropriately selected according to a number of considerations. First, the current that is programmed to go through the patient will generate a voltage $V_{PATIENT}$ across the patient. Then, in order to make the current source work, the voltage compliance $V_{COMP}$ of the current source must be appropriately set. In the case of FIG. 4, the voltage compliance $V_{COMP}$ is the voltage $V_{R1}$ across the resistor $R_1$ plus the minimum operating voltage $V_T$ of the low side transistor $Q_2$. Accordingly, the minimum voltage $V_{HV}$ across the capacitor $C_1$ is defined by the relation:

$$V_{HV}(\min.) = V_{PATIENT} + V_{COMP} \quad (2)$$

The higher $V_{HV}$ is above $V_{HV}$ (min.), the closer the current source will approach an ideal current source. Another consideration in setting $V_{HV}$ is power consumption.

The amount of current $I_{R1}$ can be varied by varying the voltage $V_{DRIVE}$ or by switching in different resistors, e.g., in series with or for $R_1$. From an implementation point of view, it is less attractive to switch in a resistor because such switching requires adding transistors or other switching devices. It is more efficient to simply vary the voltage $V_{DRIVE}$. Suitable logic circuitry may be provided to select the value of $V_{DRIVE}$. A DAC (digital to analog converter) is one example of such logic circuitry. As those skilled in the art will appreciate, a DAC is a circuit that generates different voltages in response to corresponding digital codes provided to it. Such a DAC could be used to drive either an input of the op-amp A (as illustrated in FIG. 4) or the input (gate) of the transistor $Q_1$. As noted above, an advantage of the op-amp A is that it removes the $V_T$ term from the $V_{HV}$ equation. Particular parameter ranges for circuitry as configured in FIGS. 3 and 4 include 1 to 50 ohms for the resistance $R_1$ and 1 to 20 volts for a $V_{DRIVE}$ resulting in a current ranging from 0 to 500 milliamps.

Figure 5:
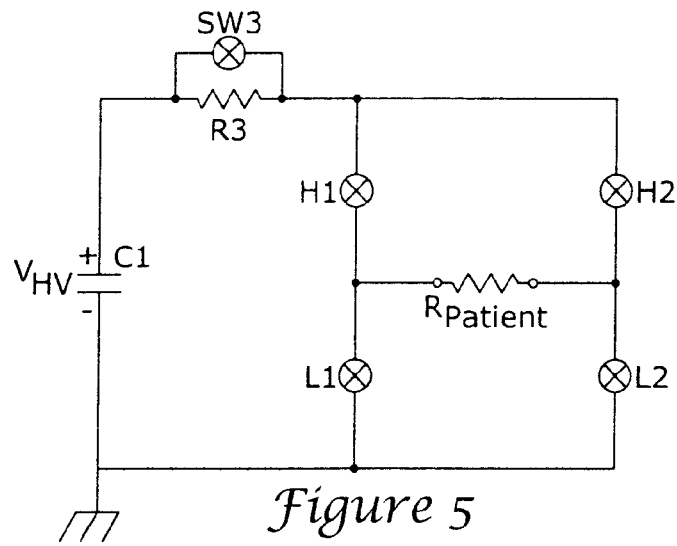
FIGS. 5 and 6 schematically illustrate high side current controlling circuits.

Another illustrative circuit for implementing a current source is illustrated in FIG. 5. This circuit employs a resistor $R_3$ connected between the high voltage capacitor $C_1$ and the high side switches $H_1$, $H_2$. The resistor $R_3$ is switched out of the circuit by a switch $SW_3$ for defibrillator operation and into the circuit for pacing.

The circuit of FIG. 5 is somewhat more energy wasteful but will work with the use of a high voltage switch for $SW_3$. In the circuit of FIG. 5, the switches $H_1$, $H_2$, $L_1$, $L_2$ are manipulated so as to place the resistor $R_3$ in series with the output. The amount of current may then be selected by the voltage to which the capacitor $C_1$ is charged. As an example, assuming the patient resistance $R_{PATIENT}$ varies from 30-150 ohms, selecting a resistor $R_3$ of anywhere from 500-5000 ohms, i.e., a resistance that is much larger than that of the patient, results in an approximation of an ideal current source. The approximation is:

$$i = V_{HV}R_3 + R_{PATIENT} \quad (3)$$

Figure 6:
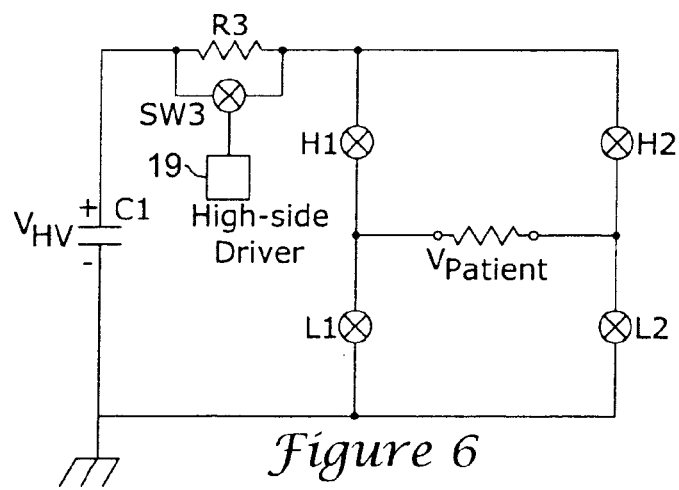

While creation of a current source according to FIG. 5 is relatively easy, switching the circuit to the defibrillation mode is more complex. As shown in FIG. 6, a high voltage switch $SW_3$ is connected across the series resistor $R_3$ to switch $R_3$ out of the circuit in order to enter the defibrillation mode. Since the high voltage switch $SW_3$ is a floating switch, a high side driver 19 is also needed. These considerations render the circuit of FIG. 6 more difficult to implement in an implantable device.

In contrast, the circuits of FIGS. 3 and 4 require a switch, e.g., $SW_1$ to switch to the defibrillation mode, but the switch $SW_1$ does not have to be a high voltage switch.

Instead, the switch SW.sub.1 need only be a smaller, low voltage device having the capacity to pass the defibrillation current. In an illustrative circuit, there may be on the order of only 10 volts across SW.sub.1, which is advantageous.

Thus, only a low voltage switch need be used in the circuits of FIGS. 3 and 4. No low voltage driver is necessary since the switch SW.sub.1 is referenced to ground and can therefore be driven directly. A high side driver circuit is unnecessary. In either of the circuits of FIG. 3 or FIG. 4, the voltage V.sub.DRIVE is preferably implemented by a DAC, either connected to directly drive the resistor R.sub.1 (FIG. 3) or to drive the resistor R.sub.3 through an op-amp A (FIG. 4).

Provision of a constant current has the advantage of maintaining a constant current density across the heart, irrespective of the electrode interface impedance.

Figure 7:
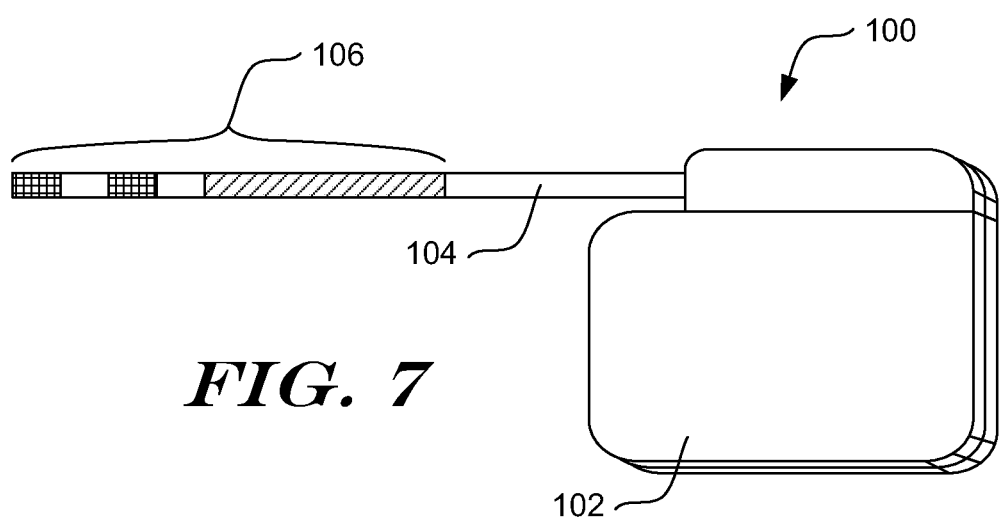
FIG. 7 is an illustrative example of an implantable cardiac device.

FIG. 7 illustrates an implantable cardiac device 100. The implantable cardiac device includes a housing 102 for containing the operational circuitry of the device. Attached to the housing 102 is a lead 104 carrying a plurality of electrodes 106. The implantable cardiac device 100 is merely illustrative of one design for an implantable device. The housing 102 may, if desired, be an active housing having an electrode for stimulus delivery or sensing. Other details of the implantable cardiac device 100 are found in U.S. Pat. No. 6,721,597, which is incorporated herein by reference.

While the present invention has been described above in terms of specific embodiments, it is to be understood that the invention is not limited to the disclosed embodiments. On the contrary, the following claims are intended to cover various modifications and equivalent methods and structures included within the spirit and scope of the invention.

What is claimed is:

1. An implantable cardiac stimulus system comprising:
   implantable electrodes for the delivery of electrical stimulus to a patient;
   operational circuitry including at least an H-bridge circuit comprising a high side and a low side, wherein the H-bridge circuit comprises first and second legs connected between the high side and the low side thereof, wherein the first leg of the H-bridge circuit comprises first and second current switching elements and the second leg of the H-bridge circuit comprises third and fourth current switching elements, the H-bridge comprising output nodes for coupling to patient tissue via the implantable electrodes, wherein a first output node is located on the first leg between the first and second current switching elements and a second output node is located on the second leg between the third and fourth current switching elements, the operational circuitry further comprising a constant current circuit connected to the low side of the H-bridge circuit and
   a canister for housing at least the battery and operational circuitry;
   wherein the first and fourth current switching elements define a first pair of current switching elements;
   wherein the operational circuitry is configured to select the first pair of current switching elements to generate a stimulus of a first polarity for application via the first and second output nodes; and
   wherein the constant current circuit comprises a bypass switch and a pacing resistor in parallel with one another and coupled to the low side of the H-bridge;
   wherein the operational circuitry is configured to close the bypass switch to deliver a defibrillation output, and to open the bypass switch to force current from the low side of the H-bridge through the pacing resistor to deliver a pacing output and
   wherein the constant current circuit is configured to control operation of the fourth current switching element by monitoring a voltage across the pacing resistor during a stimulus of the first polarity to force the stimulus to be a substantially constant current pacing stimulus.

2. The implantable system of claim 1 wherein:
   in the first leg of the H-bridge, the first current switching element links the high side of the H-bridge to the first output node and the second current switching element links the low side of the H-bridge to the first output node;
   in the second leg of the H-bridge, the third current switching element links the high side of the H-bridge to the second output node and the fourth current switching element links the low side of the H-bridge to the second output node;
   the constant current circuit includes an amplifier for generating a control signal output to the fourth switching element.

3. The implantable system of claim 2 wherein the operational circuitry is configured to generate the substantially constant current pacing therapy by applying a first voltage to the high side of the H-bridge, closing the first switch, and applying the control signal output to the fourth switch.

4. The implantable system of claim 3 wherein the operational circuitry further comprises a therapy circuit with a high power capacitor for use in delivering either pacing or defibrillator therapy, such that the first voltage is received from the high power capacitor.

* * * * *